United States Patent
Yang

(10) Patent No.: US 11,136,382 B2
(45) Date of Patent: Oct. 5, 2021

(54) ANTIBODIES AND ANTIBODY FRAGMENTS FOR BINDING TO NAV1.9 POLYPEPTIDES AND METHODS FOR USING SAME TO TREAT PAIN-RELATED DISEASE

(71) Applicant: POPULAS BIOPHARMACEUTICAL (WUHAN) LIMITED, Wuhan (CN)

(72) Inventor: Daichang Yang, Wuhan (CN)

(73) Assignee: POPULAS BIOPHARMACEUTICAL (WUHAN) LIMITED, Wuhan (CN)

( * ) Notice: Subject to any disclaimer, the term of this patent is extended or adjusted under 35 U.S.C. 154(b) by 47 days.

(21) Appl. No.: 16/657,515

(22) Filed: Oct. 18, 2019

(65) Prior Publication Data

US 2020/0157198 A1 May 21, 2020

Related U.S. Application Data

(63) Continuation of application No. PCT/CN2018/075603, filed on Feb. 7, 2018.

(30) Foreign Application Priority Data

Feb. 21, 2017 (CN) .......................... 201710093290.2

(51) Int. Cl.
*A61K 39/395* (2006.01)
*C07K 16/18* (2006.01)
*C07K 16/28* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01); *C07K 2317/624* (2013.01)

(58) Field of Classification Search
None
See application file for complete search history.

(56) References Cited

FOREIGN PATENT DOCUMENTS

WO 2014207402 A1 12/2014

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Yue, International Search Report for PCT/CN2018/075603, dated Apr. 26, 2018.

* cited by examiner

*Primary Examiner* — Christine J Saoud
*Assistant Examiner* — Jon M Lockard
(74) *Attorney, Agent, or Firm* — Greer, Burns & Crain, Ltd.; Gregory P. Einhorn

(57) ABSTRACT

The present invention provides an antibody or antibody fragment thereof for a targeted cytomembrane voltage-gated sodium channel α subunit Nav1.9. The specific binding target is a S3-4 ring of a voltage sensor paddle of a domain II of the voltage-gated sodium channel α subunit. The antibody or antibody fragment thereof is able to inactivate a voltage sensor valve, to make sodium ions unable to enter nerve cells normally, thereby achieving the effect of treating and relieving pains.

8 Claims, 2 Drawing Sheets
Specification includes a Sequence Listing.

SEQUENCE LISTING

<160> NUMBER OF SEQ ID NOS: 13

<210> SEQ ID NO 1
<211> LENGTH: 14
<212> TYPE: PRT
<213> ORGANISM: Artificial
<220> FEATURE:
<223> OTHER INFORMATION: Polypeptide specifically binding to antibody

<400> SEQUENCE: 1

Leu Asn Ser Phe Ser Asn Glu Glu Arg Asn Gly Asn Leu Glu
1               5                   10

<210> SEQ ID NO 2
<211> LENGTH: 138
<212> TYPE: PRT
<213> ORGANISM: Artificial
<220> FEATURE:
<223> OTHER INFORMATION: Heavy chain variable region

<400> SEQUENCE: 2

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Arg Asn Gly Arg Ile Asn Gln Asn
65                  70                  75                  80

Glu Lys Phe Lys Ser Lys Ala Thr Leu Thr Val Ala Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ser Arg Gly Gly Gly Ser Ser Ala Glu Gly Gly Tyr Trp
        115                 120                 125

Gly Gln Gly Thr Thr Leu Thr Val Ser Ser
        130                 135

<210> SEQ ID NO 3
<211> LENGTH: 131
<212> TYPE: PRT
<213> ORGANISM: Artificial
<220> FEATURE:
<223> OTHER INFORMATION: Light chain variable region

<400> SEQUENCE: 3

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Asp Trp Tyr Leu Gln Lys Pro
    50                  55                  60

Gly Gln Ser Pro Lys Leu Leu Ile Tyr Lys Val Phe Asn Arg Leu Ser
65                  70                  75                  80

Gly Val Pro Asp Arg Phe Ser Gly Ser Gly Ser Gly Thr Asp Phe Thr
                85                  90                  95

```
Leu Lys Ile Ser Arg Val Glu Ala Glu Asp Leu Gly Val Tyr Tyr Cys
            100                 105                 110

Phe Gln Gly Ser His Val Pro Leu Thr Phe Gly Ala Gly Thr Lys Leu
        115                 120                 125

Glu Leu Gln
    130

<210> SEQ ID NO 4
<211> LENGTH: 5
<212> TYPE: PRT
<213> ORGANISM: Artificial
<220> FEATURE:
<223> OTHER INFORMATION: CDRH1

<400> SEQUENCE: 4

Ser Tyr Trp Met His
1               5

<210> SEQ ID NO 5
<211> LENGTH: 17
<212> TYPE: PRT
<213> ORGANISM: Artificial
<220> FEATURE:
<223> OTHER INFORMATION: CDRH2

<400> SEQUENCE: 5

Glu Ile Asn Pro Arg Asn Gly Arg Ile Asn Gln Asn Glu Lys Phe Lys
1               5                   10                  15

Ser

<210> SEQ ID NO 6
<211> LENGTH: 10
<212> TYPE: PRT
<213> ORGANISM: Artificial
<220> FEATURE:
<223> OTHER INFORMATION: CDRH3

<400> SEQUENCE: 6

Gly Gly Gly Ser Ser Ala Glu Gly Gly Tyr
1               5                   10

<210> SEQ ID NO 7
<211> LENGTH: 16
<212> TYPE: PRT
<213> ORGANISM: Artificial
<220> FEATURE:
<223> OTHER INFORMATION: CDRL1

<400> SEQUENCE: 7

Arg Ser Ser Gln Ser Ile Val His Ser Asn Gly Asn Thr Tyr Leu Asp
1               5                   10                  15

<210> SEQ ID NO 8
<211> LENGTH: 7
<212> TYPE: PRT
<213> ORGANISM: Artificial
<220> FEATURE:
<223> OTHER INFORMATION: CDRL2

<400> SEQUENCE: 8

Lys Val Phe Asn Arg Leu Ser
1               5

<210> SEQ ID NO 9
```

```
<211> LENGTH: 9
<212> TYPE: PRT
<213> ORGANISM: Artificial
<220> FEATURE:
<223> OTHER INFORMATION: CDRL3

<400> SEQUENCE: 9

Phe Gln Gly Ser His Val Pro Leu Thr
1               5

<210> SEQ ID NO 10
<211> LENGTH: 414
<212> TYPE: DNA
<213> ORGANISM: Artificial
<220> FEATURE:
<223> OTHER INFORMATION: DNA sequence of heavy chain variable region

<400> SEQUENCE: 10
atgggatgga gctatatcat cctctttttg gtagcaacag ctacagatgt ccactcccag      60
gtccaactgc agcagcctgg ggctgaactg gtgaagcctg ggcttcagt gaagctgtcc      120 tgcaaggctt ctggctacac cttcaccagc tactggatgc actgggtgaa gcagaggcct    180
ggacaaggcc ttgagtggat tggagagatt aatcctagga acggtcgtat taaccagaat    240
gagaagttca gagcaaggc cacactgact gtagccaaat cctccagcac ggcctacatg     300
caactcagca gcctgacatc tgaggactct gcggtctatt actgttcaag aggggggcggt   360 agtagcgcgg aggggggcta ctggggccaa ggcaccactc tcacagtctc ctca          414

<210> SEQ ID NO 11
<211> LENGTH: 393
<212> TYPE: DNA
<213> ORGANISM: Artificial
<220> FEATURE:
<223> OTHER INFORMATION: DNA sequence of light chain variable region

<400> SEQUENCE: 11
atgaagttgc ctgttaggct gttggtgctg atgttctgga ttcctgcttc cagcagtgat      60
gttttgatga cccaaactcc actctccctg cctgtcagtc ttggagatca agcctccatc    120
tcttgcagat ctagtcagag cattgtacat agtaatggaa cacctattt agattggtac     180 ctgcagaaac caggccagtc tccaaagctc ctgatataca agttttcaa ccgactttct     240 ggggtcccag acaggttcag tggcagtgga tcagggacag atttcacact caagatcagc    300
agagtggagg ctgaggatct gggagtttat tactgctttc aaggttcaca tgttcctctc    360
acgttcggtg ccgggaccaa gctggagctg caa                                 393

<210> SEQ ID NO 12
<211> LENGTH: 414
<212> TYPE: RNA
<213> ORGANISM: Artificial
<220> FEATURE:
<223> OTHER INFORMATION: RNA sequence of heavy chain variable region

<400> SEQUENCE: 12
augggaugga gcuauaucau ccucuuuuug guagcaacag cuacagaugu ccacucccag      60
guccaacugc agcagccugg ggcugaacug gugaagccug ggcuucagu gaagcuguuc     120 ugcaaggcuu cuggcuacac cuucaccagc uacuggaugc acuggugaa gcagaggccu     180 ggacaaggcc uugagugau uggagagauu aauccuagga acggucguau uaaccagaau    240
gagaaguuca gagcaaggc cacacugacu guagccaaau ccuccagcac ggccuacaug     300
```

```
caacucagca gccugacauc ugaggacucu gcggucuauu acuguucaag aggggggcggu    360 aguagcgcgg agggggggcua cuggggccaa ggcaccacuc ucacagucuc cuca          414

<210> SEQ ID NO 13
<211> LENGTH: 393
<212> TYPE: RNA
<213> ORGANISM: Artificial
<220> FEATURE:
<223> OTHER INFORMATION: RNA sequence of light chain variable region

<400> SEQUENCE: 13
augaaguugc cuguuaggcu guuggugcug auguucugga uuccugcuuc cagcagugau     60
guuuugauga cccaaacucc acucucccug ccugucaguc uuggagauca agccuccauc    120
ucuugcagau cuagucagag cauuguacau aguaauggaa acaccuauuu agauuggua c   180 cugcagaaac caggccaguc uccaaagcuc cugauauaca aaguuuucaa ccgacuuucu    240
ggggucccag acaguucag uggcagugga ucagggacag auuucacacu caagaucagc     300
agaguggagg cugaggaucu gggaguuuau uacugcuuuc aagguucaca uguuccucuc    360
acguucggug ccgggaccaa gcuggagcug caa                                 393
```

ANTIBODIES AND ANTIBODY FRAGMENTS FOR BINDING TO NAV1.9 POLYPEPTIDES AND METHODS FOR USING SAME TO TREAT PAIN-RELATED DISEASE

RELATED APPLICATIONS

This United States utility patent application is a continuation of PCT International Application PCT/CN2018/075603, filed Feb. 7, 2018, which claims benefit of priority to Chinese Patent Application No. 201710093290.2, filed Feb. 21, 2017, now expired. The aforementioned applications are expressly incorporated herein by reference in their entirety and for all purposes.

FIELD OF THE INVENTION

The present invention relates to a Nav1.9 target polypeptide, an antibody and/or antibody fragment which binds to the polypeptide, and a pharmaceutical composition comprising the antibody and/or antibody fragment for the treatment of pain, itching and cough.

BACKGROUND OF THE INVENTION

Pain begins with the nociceptors of the peripheral nervous system that are widely distributed in the skin, muscles, joints and visceral tissues of the whole body as a kind of free nerve ending, and can convert thermal, mechanical or chemical stimuli into action potentials, transmit them to the cell body in the dorsal root ganglia (DRG) through nerve fibers and ultimately to the advanced nerve center, thereby causing pain. The generation and conduction of action potentials in neurons in turn depend on the voltage-gated sodium channels (VGSCs) located on the cytomembrane. When the cytomembrane is depolarized, the sodium ion channel is activated. The channel is opened, causing sodium ion influx, and further depolarizing the cytomembrane, resulting in the generation of an action potential, and thus causing pain due to the abnormal action potential. Therefore, inhibition of abnormal sodium ion channel activity contributes to the treatment and alleviation of pain.

Figure 1:
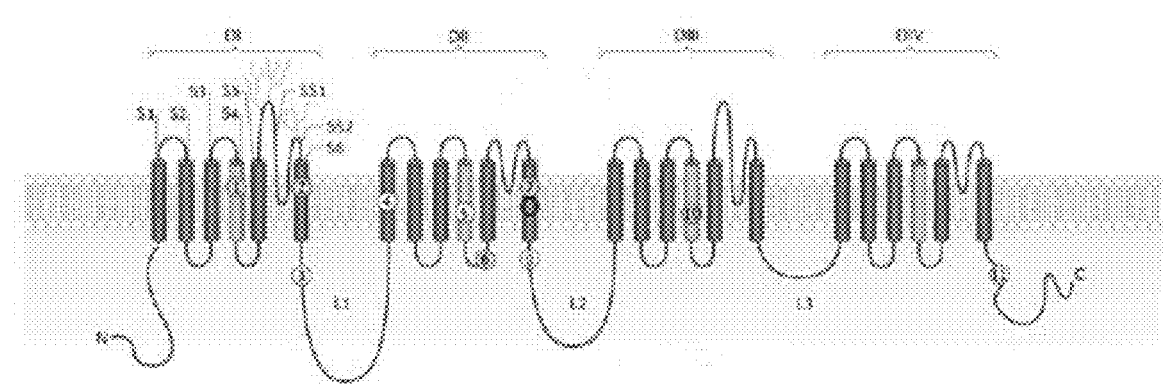

Voltage-gated sodium channels are widely found on the cytomembranes of neuron and skeletal muscle cells, which are a class of transmembrane glycoprotein complexes composed of an α subunit and several β subunits. The α subunit is a functional carrier of the sodium ion channel, consisting of 1700 to 2000 amino acids, forming 4 domains (I-IV), each of which contains 6 transmembrane segments (S1-S6) (FIG. 1). The domains are connected by some large intracellular loops, and the fragments are connected by small extracellular or intracellular loops. Among them, S4 is rich in basic amino acid residues and is considered to be a voltage-sensitive component of voltage-gated sodium ion channels. When the cytomembrane is depolarized, the positive charges on S4 can move out along the axis of S4 in a clockwise direction, change the sodium ion channel conformation and open the channel. The pore loop (P-loop) between S5 and S6 forms the extracellular portion of the micropore, which is related to the selectivity to sodium ions, while the intracellular portion of the micropore is surrounded by S6. The intracellular loop linking domains III and IV acts as an inactivation valve that can fold into the intracellular opening of the micropore, block the micropore, and inactivate the voltage-gated sodium ion channel Mutations in the L2 intimal region of domain II can result in a pain-free phenotype (Nature Genetics, 2013, 45 (11): 1399-1404).

It can be classified according to differences, nine voltage-gated sodium ion channel α subunits have been identified in mammals so far, since the amino acid sequences have a more than 50% similarity, they are considered to be from the same family, named Nav1 (Nav1.1-Nav1.9). Experiments have shown that they are expressed in large amounts in neurons, and Nav1.9 is present in the peripheral nervous system (PNS). Recent studies have shown that the subtypes of Nav1 associated with pain are mainly Nav1.3, Nav1.7, Nav1.8 and Nav1.9. Nav1.9 is an important member mainly responsible for pains. Nav1.9 is a TTX-R type having the coding gene of SCN11A and is mainly distributed in the DRG neurons, trigeminal ganglia and intestinal myenteric neurons for feeling hurt. The activation voltage of Nav1.9 is close to the resting membrane potential of neurons (−60∼−70 mV), with a dynamic characteristic of slow activation and slow deactivation, so it can produce a longer-lasting TTX-R current, which indicates that Nav1.9 can amplify and prolong the response of neurons to subthreshold depolarization, and trigger an action potential. In the human body, the activation voltage of Nav1.9 is −80 mV. Recently, in the pain-free patients, the amino acid mutation at position 811 in Nav1.9 has produced painless symptoms. Further research on the gene indicates that it is one of the sodium ion channels mainly responsible for pains.

SUMMARY OF THE INVENTION

The first object of the present invention is to provide a voltage sensor paddle region of domain II in Nav1.9 as a target, obtaining a monoclonal antibody by using the polypeptide as an antigen. By binding the specific antibody to its target, the VGSCs ion channels can be closed, thereby inhibiting pains. The polypeptide has the sequence as shown in SEQ ID NO:1, or a structurally similar derivative sequence having 80%, 85%, 90% or 95% homology to the polypeptide.

The second object of the present invention is to provide an antibody and antibody fragment thereof that specifically recognize the target, comprising a heavy chain variable region (VH) having the sequence as shown in SEQ ID NO:2 or a structurally similar derivative sequence with 80%, 85%, 90% or 95% homology to the polypeptide; and a light chain variable region (VL) having the sequence as shown in SEQ ID NO:3 or a structurally similar derivative sequence with 80%, 85%, 90% or 95% homology to the polypeptide; Also, the three CDR sequences contained in the heavy chain variable region (SEQ ID NO:2) and/or the three CDR sequences contained in light chain variable region (SEQ ID NO:3) can be taken and transplanted to obtain a CDR-grafted antibody and antibody fragment thereof. The CDR sequences in the heavy chain variable region comprise CDRH1 as shown in SEQ ID NO.4, CDRH2 as shown in SEQ ID NO.5, and CDRH3 as shown in SEQ ID NO.6; the CDR sequences in the light variable region comprise CDRL1 as shown in SEQ ID NO.7, CDRL2 as shown in SEQ ID NO.8, and CDRL3 as shown in SEQ ID NO.9.

The light chain constant region of the antibody and antibody fragment thereof may be selected from a κ chain or a λ chain, and the heavy chain constant region thereof may be selected from the group consisting of IgM, IgD, IgG I, IgA, IgE, etc.

The species sources of the light chain constant region and the heavy chain constant region may be selected from the group consisting of human antibody constant region, bovine antibody constant region, sheep antibody constant region, canine antibody constant region, porcine antibody constant region, feline antibody constant region, equine antibody constant region, and scorpion antibody constant region.

The antibody and antibody fragment thereof may be in a structural form selected from the group consisting of a full antibody, Fab, F(ab')2, dsFv, scFv, a diabody, a minibody, a bispecific antibody, a multispecific antibody, a chimeric antibody, a CDR-graft antibody.

The antibody and antibody fragment thereof are preferably an antibody or antibody fragment in monoclonal form.

The third object of the present invention is to provide a pharmaceutical composition comprising the above antibody or antibody fragments thereof as an active ingredient. The pharmaceutical composition has an analgesic effect and an effect of increasing pain threshold, and can treat pains, itching and cough.

According to the first aspect of the invention, based on the crystal structural model of Nav1.9, a suitable polypeptide is screened as an antigen in the voltage sensor paddle region of domain II of the voltage sensor valve of Nav1.9. Through hydrophilicity and antigenicity analysis, a polypeptide with good hydrophilicity and high antigenicity is screened, having the amino acid sequence of LNSFSNEERNGNLE (SEQ ID NO.1).

According to the second aspect of the invention, the first step is to prepare a monoclonal cell line that secrets the antibody.

The above polypeptide is chemically synthesized (addition of a cysteine at its C-terminus), designated as C8079BB030-1, which is coupled to the carrier protein KLH, and then used to immunize the BALB/c mouse to stimulate the body for several times to produce an immune response, thereby producing an polyclonal antibody, for blood tests, ELISA tests and evaluations.

The polyclonal antibody titer of the immunized animals was evaluated by ELISA through antigen-antibody reaction. Based on the antibody titer of the immunized animal and the specificity of the neural tissues, two animals #1955, #1958 were finally selected for cell fusion. The spleen cells of the two animals were electrofused with mouse myeloma cells (SP2/0), and then cultured after fusion, and the positive cell lines were screened on the screening medium. The titer and tissue specificity of the secreted antibody were tested, and the hybridoma cell line was screened using the polypeptide C8079BB030-1 as an antigen. According to the ELISA test results, 5A2, 9D2, and 15F5 were selected for subcloning by limiting dilution method.

After another ELISA test and specificity test, only 5A2 cells were specific and positive to nerve tissues, and finally cells 5A2F9-1 and 5A2F9-4 were selected for cell cryopreservation.

The second step is to sequence the variable region of the native antibody, extract the total RNA of the 5A2F9-4 cell line, synthesize the cDNA, establish a cDNA library, and perform variable region sequencing. Amplification of a polynucleotide sequence encoding a variable region of an antibody can comprise integrating the DNA sequences encoding VH and VL (which can also be manipulated by RNA sequences encoding variable regions) into the same vector, or integrating them into vectors, respectively, and transfecting a suitable host cell with the above vector; and then subjecting it to sequencing analysis. The sequencing results show that the DNA sequence encoding the VH is shown in SEQ ID NO:10, and the DNA sequence encoding the VL is shown in SEQ ID NO:11.

The third step is to construct a genetically engineered antibody, and according to different needs, introduce the above DNA sequences encoding VH and VL (or encoding the CDR in VH and encoding the CDR in VL) into a suitable host for antibody expression, and verify the antibody effect.

The present invention is addressed to the shortcoming of clinical application of chemical small molecules (such as carbamazepine, lidocaine, mexiletine, etc.) as a voltage-gated sodium ion channel inhibitor for the treatment of pains, due to lacking of sufficient selectivity for voltage-gated sodium ion channel subtypes, thereby producing cardiotoxicity and central nervous side effects. The biological macromolecules targeting an antibody against voltage sensors of the Nav1.9 voltage-gated sodium ion channel can be used to inactivate the voltage sensor valve, make sodium ions unable to enter nerve cells normally, thereby achieving the effect of treating and relieving pains. Due to their good targeting, they can overcome the side effects caused by chemical small molecule drugs.

DESCRIPTION OF THE INVENTION

FIG. 1: Structure diagram of the sodium ion channel Nav1.9

Figure 2:
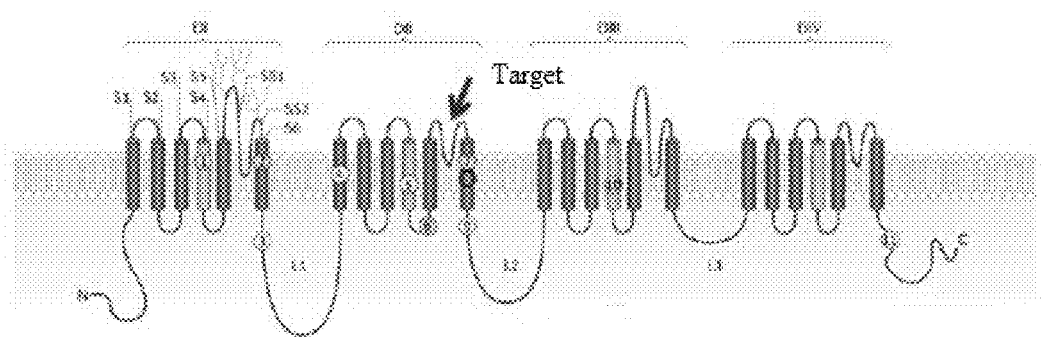

FIG. 2: Target design diagram of the sodium ion channel Nav1.9

Figure 3:
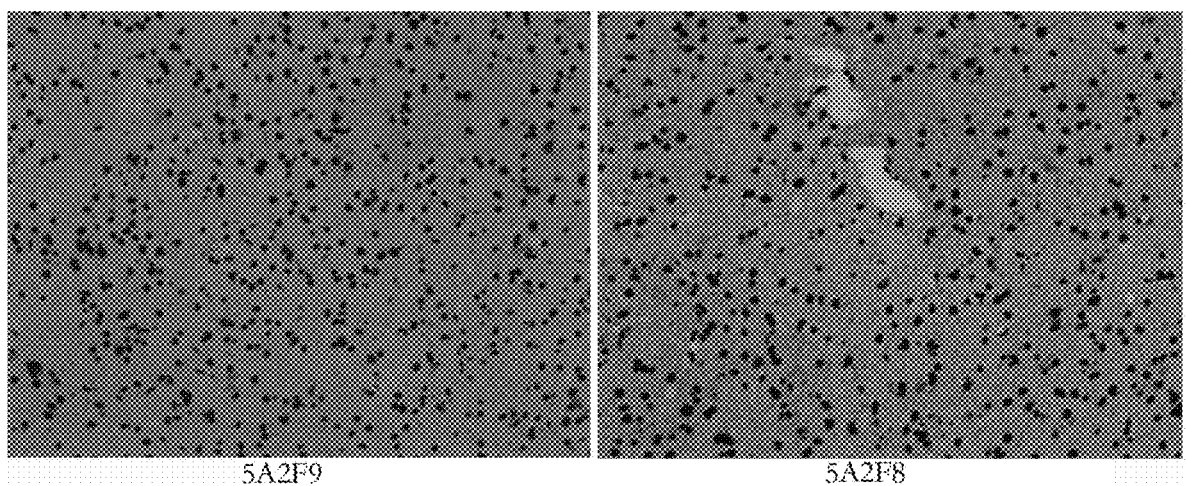
Figure 5:
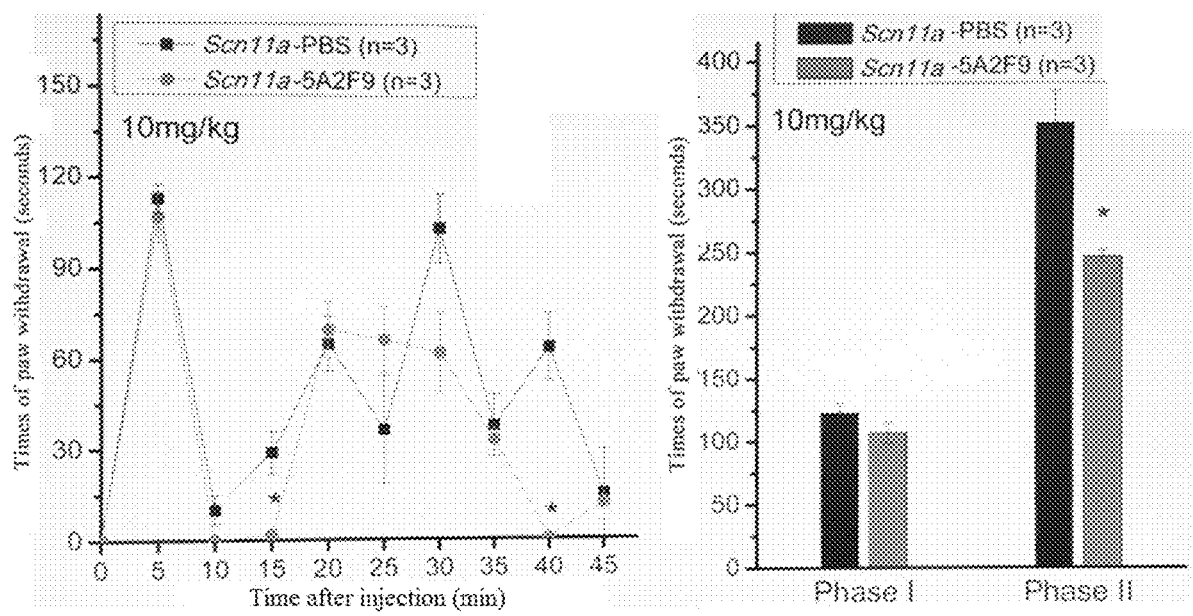

FIG. 3: Specificity of antibodies secreted by 5A2F8 and 5A2F9 cell lines to neural tissue FIG. 4: Verification of antibody specificity by Western blotting ND7/23:HA-hNav1.9 refers to ND7/23 cells transfected with HA-hNav1.9 plasmid;

COS-7:HA-M refers to COS-7 cells transfected with HA tag as negative control;

ND7/23 refers to untransfected cells as negative control;

FIG. 5: Analgesic effect of 5A2F9-4 antibody on 5% Formalin-induced acute inflammatory pain in wild type mice.

DETAILED DESCRIPTION OF THE INVENTION

The invention is illustrated, but not limited by the following detailed description of the preferred embodiments of the invention.

Material sources:

The materials and reagents used below are commercially available unless otherwise stated.

Example 1 [Synthesis of Antigen]

According to the amino acid sequence (GenBank No. NP_001274152) and the crystal structural model of Nav1.9, the hydrophilicity and antigenicity analysis was performed in the vicinity of the pain site 811 to screen the sequence LNSFSNEERNGNLE, the hydrophilicity and antigenicity of which met the requirements of the antigen. The LNSFS-NEERNGNLEC polypeptide was synthesized using a fully automated synthesizer.

Specific steps were as follows:

(1) attaching —COOH of the first AA to Cl-Resin with DIEA, and then blocking the unreacted functional groups on the resin with MeOH;

(2) washing with DMF;

(3) removing the protecting group Fmoc of —NH$_2$ in the first AA with Pip to expose the —NH$_2$;

(4) washing with DMF;

(5) activating —COOH of the second AA with DIC+ HOBT, and then condensing it with —NH$_2$ in the first AA to form an amide bond;

(6) washing with DMF;
(7) removing the protecting group Fmoc of —NH$_2$ in the second AA with Pip to expose the —NH$_2$;
(8) washing with DMF;
(9) . . . repeating the steps 5-8 until exposing the —NH$_2$ of the last AA;
(10) cutting the polypeptide from the resin and removing the side chain protecting groups of all amino acids with the cleavage reagent as: trifluoroacetic acid+ethanedithiol+phenol+thioanisole+water;
(11) adding the cleavage solution into diethyl ether to precipitate the polypeptide, and centrifuging to obtain the crude peptide (C8079BB030-1);
(12) purifying with a peptide HPLC C18 preparative/analytical column, designated as C8079BB030-1, to obtain the purified polypeptide for immunizing animals.

Example 2 [Preparation of Monoclonal Cell Lines]

2.1 Animal Immunization

Freund's complete adjuvant (Sigma, F5881) and Freund's incomplete adjuvant (Sigma, F5506) were prepared. The polypeptide was coupled to the carrier protein KLH by the C-terminal —SH of polypeptide C8079BB030-1 as an immunogen.

Five 8-week-old female BALB/c (animal numbers: #1954, #1955, #1956, #1957, #1958) were selected and immunized intraperitoneally three times to stimulate the body to produce an immune response and then to produce antibodies. Primary immunization: 50 μg/each; the secondary immunization was performed after three weeks, at a dose of 50 μg/each; the third immunization was carried out 2 weeks after the second immunization at a dose of 50 μg/each; 1 week after the third immunization, blood was collected for antibody test.

2.2 ELISA Test of Animal Serum
2.2.1 Instruments and Equipments
Washing machine: Beijing Nanhua ZDMX
Microtiter-plate reader: Thermo Multiskan Ascent
2.2.2 Reagents
Coating antigen: polypeptide C8079BB030-1; coating solution: 1*PBS (pH 7.4); washing buffer: 1*PBS (pH 7.4), 0.05% PBS; the primary antibody: anti-serum after the third immunization; enzyme-labeled secondary antibody: Peroxidase-AffiniPure Goat Anti-Mouse IgG, Fcγ Fragment Specific (min X Hu, Bov, Hrs Sr Prot); TMB chromogenic solution; stop solution: 1 M hydrochloric acid.

The specific method was as follows:

(1) Coating: The antigen was diluted to 1 μg/ml with the coating solution, mixed and then added to the microtiter-plate at 100 μl per well, covered with the cover film, and placed at 4° C. overnight.

(2) Blocking: The microtiter-plate was taken out to discard the coating solution, added with the blocking solution, covered with the cover film, and incubated at 37° C. for 0.5 h.

(3) Addition of primary antibody: The anti-serum after the third immunization was first diluted 1000-fold, and then subjected to doubling dilution for 9 gradients, covered with the cover film, and incubated at 37° C. for 1 h.

(4) Addition of secondary antibody: The enzyme-labeled microtiter-plate was taken out to discard the solution inside, added with the diluted secondary antibody at a concentration of 0.033 μg/ml, covered with the cover film, and incubated at 37° C. for half an hour.

(5) Color development: The enzyme-labeled microtiter-plate was taken out to discard the solution inside, added with the chromogenic solution to develop the color at 25° C. for 13 minutes.

(6) Stop of Reaction: The stop solution was added to stop the reaction.

(7) The value was read at 450 nm on a microtiter-plate reader immediately after the addition of the stop solution. The maximum dilution corresponding to the well having an OD value of more than 2.1 times the OD value of the set negative control was determined as the titer of the sample, and the test results are as shown in Table 2. NC is a negative control of unimmunized serum, and the initial dilution factor is 1:1,000. The anti-serum after the third immunization was tested, the anti-serum titers of animal number #1955, #1956 were 1:128,000; the anti-serum titer of animal number #1954 was 1:64,000; the anti-serum titers of the remaining 2 animals (#1957, #1958) were 1:16,000.

TABLE 2

Test results of serum ELISA after the third immunization:

| Animal No. | Dilution factor | No. 1954 | No. 1955 | No. 1956 | No. 1957 | No. 1958 |
| --- | --- | --- | --- | --- | --- | --- |
| Negative control | 1:1,000 | 0.072 | 0.066 | 0.086 | 0.088 | 0.104 |
| Dilution 1 | 1:1,000 | 3.219 | 2.88 | 3.067 | 2.915 | 2.74 |
| Dilution 2 | 1:2,000 | 3.125 | 2.733 | 2.847 | 2.579 | 2.322 |
| Dilution 3 | 1:4,000 | 3.087 | 2.714 | 2.57 | 2.22 | 2.031 |
| Dilution 4 | 1:8,000 | 2.47 | 2.541 | 2.456 | 1.677 | 1.565 |
| Dilution 5 | 1:16,000 | 2.135 | 2.314 | 2.352 | 1.105 | 1.068 |
| Dilution 6 | 1:32,000 | 1.73 | 1.942 | 1.988 | 0.675 | 0.647 |
| Dilution 7 | 1:64,000 | 1.242 | 1.578 | 1.553 | 0.384 | 0.417 |
| Dilution 8 | 1:128,000 | 0.843 | 1.077 | 1.052 | 0.207 | 0.233 |
| Dilution 9 | 1:256,000 | 0.471 | 0.654 | 0.649 | 0.162 | 0.155 |
| Dilution 10 | 1:512,000 | 0.296 | 0.373 | 0.387 | 0.119 | 0.118 |
| Dilution 11 | Blank control | 0.072 | 0.072 | 0.072 | 0.072 | 0.072 |
| Titer | | 1:512,000 | 1:512,000 | 1:512,000 | 1:256,000 | 1:256,000 |

2.3 Cell Fusion and Screening of Hybridoma Cell Lines 2.3.1 Cell Fusion:

According to the ELISA test results of Example 2.2, combined with the tissue specificity results, two animals #1955, #1958 were selected for final immunization, and three days later the spleen cells of the two animals were fused with tumor cells. The mouse myeloma cells (SP2/0) and spleen cells were electrofused in a 1:3 ratio and the fused cells were plated into 15 feeder cell plates using HAT medium, and cultured in a $CO_2$ incubator.

2.3.2 Screening of Hybridoma Cell Lines:

After the fused cells were cultured for 7-10 days, the whole medium was replaced and ELISA test was carried out after 4 hours of the medium replacement.

The specific materials and procedures of ELISA were the same as that of ELISA test of animal serum in 2.2.

First ELISA Screening:

There is a total of fifteen 96-well microtiter-plate. Well 15H12 (well H12 of the 15th full plate) was set as positive control, a 1000-fold diluted solution of fused animal serum was added, and the OD value was determined to be 2.386; Well 15G12 (well G12 of the 15th full plate) was set as negative control, a blank medium was added, and the OD value was determined to be 0.085. The results showed that 68 out of 1440 cells in the fifteen 96-well microtiter-plates had an OD value of more than 1.0.

Second ELISA Screening:

The clones with OD>1.0 of the 68 single-well cells screened from the first screening were subjected to a second test (same as the above test method). The results showed that the OD values of 20 cell lines were close to that of the positive control, having an OD value of more than 2.1. They were 2D11, 3E2, 3F3, 3F11, 5A2, 5B4, 5E4, 7C8, 9B10, 9D2, 9G9, 10A7, 10C1, 11A2, 11B6, 12D12, 13B4, 13H7, 15F5, 15H3, respectively.

Third ELISA Screening:

20 lines with higher OD values from the second screening were selected for positive confirmation test (same as the above test method). The results showed that only 10 cell stains had an OD value of more than 2.0, and they were 2D11, 3E2, 3F3, 5A2, 5B4, 7C8, 9B10, 9D2, 13B4 and 15F5. The above 10 cell lines were expanded into 24-well microtiter-plates, and 2 ml of supernatant of each line was collected for next confirmation step.

2.3.3. Cytological Specificity Confirmation

In order to confirm whether these cell lines have specificity to nerve tissues, the supernatants of a total of 10 cell lines of 2D11, 3E2, 3F3, 5A2, 5B4, 7C8, 9B10, 9D2, 13B4, and 15F5 were subjected to immunohistochemical examination. The specific experimental methods were as follows:

2.3.3.1 Tissue Dehydration Treatment:

The human nerve tissue was taken for dehydration treatment, and the dehydration treatment was carried out by Leica ASP300S. The specific process was as follows:

The tissues was dehydrated with 70%, 85%, 90%, anhydrous ethanol for 30 minutes, respectively; then dehydrated twice with anhydrous ethanol for 60 minutes each time; then treated with clearing agent for 30 minutes, then treated with clearing agent twice for 60 minutes each time; and then treated 3 times with paraffin, for 60 minutes, 120 minutes and 180 minutes, respectively, and then subjected to embedding operation using a Leica EG1150 embedding machine, to prepare a wax block, which was cut into sections with a thickness of 4 µm.

2.3.3.2 In Situ Hybridization:

The nerve tissue sections were baked at 85° C. for 20 min; treated 3 times with a dewaxing agent for 1 minute each time; dewaxed 3 times with anhydrous alcohol for 1 minute each time; washed 3 times with water for 1 minute each time; thermal repaired with ER2 (pH=9 buffer solution) for 20 minutes, cooled for 12 minutes, then washed 3 times with water for 1 minute each time; then blocked for 30 minutes; washed 3 times with water for 1 minute each time; added with the supernatant of the cell line culture and incubated for 30 minutes, washed 3 times with water for 1 minute each time; incubated for 8 minutes with enhancer, washed 3 times with water for 2 minutes each time, added with secondary antibody and incubated for 8 minutes; washed 3 times with water for 2 minutes each time; developed color with DAB for 8 minutes; washed 3 times with water for 1 minute each time, stained with hematoxylin for 10 minutes; washed 3 times with water for 1 minute each time, dehydrated with alcohol, air-dried and sealed. Observations were performed using an Olympus optical microscope.

It was found by optical microscopy that the specificity and hybridization signals of the secreted antibodies of three cell lines in the nerve tissues met the requirements. The results are shown in the following table.

| Clone No. | Specificity | Hybridization signal |
|---|---|---|
| 5A2 | * * | * * |
| 9D2 | * * | * |
| 15F5 | * * | * |

2.3.4 Subcloning

According to the results of the cytology test of Example 2.3.3, 5A2, 9D2, and 15F5 were selected for subcloning. Three cell lines were subcloned by limiting dilution method, and the three cell lines were plated into a 96-well feeder cell plate. After 7-10 days of culture, 12 monoclonal clones were selected from each line for ELISA test (same as above test method). The results showed that 14 clones such as 5A2E9, 5A2F8, 5A2F9, 9D2A10, 9D2C9, 9D2F7, 9D2F8, 15F5B9, 15F5B11, 15F5D10, and 15F5G6 had an OD value of more than 2.2 and the others were negative. These were selected for a second confirmation and the OD values were confirmed to be more than 2.2. These positive monoclones were then expanded into a 24-well microtiter-plate and 2 ml of supernatant of each clone culture was collected for cytological confirmation. It was confirmed by tissue immunochemistry that only 5A2F8 and 5A2F9 clones were immunohistochemically positive (see FIG. 3).

Since the three clones that were immunohistochemically positive were from the same clone, 5A2F8 and 5A2F9 were selected for the second subcloning (subcloning method was the same as above). After 7-10 days of culture, 12 monoclonal wells were selected for ELISA test. The results showed that they were all positive, indicating that these were already homozygous monoclonal. Five sub-clones were randomly selected, and the supernatants were subjected to titer assay and subtype identification (Southern Biotech kit, Cat. No. ST17). The results showed that the OD values of the five clones were identical, the titer was 1:2400, and the subtypes were IgG and K. Finally, three cells, 5A2F8-5, 5A2F9-1, and 5A2F9-4, were selected for cell cryopreservation.

Example 3 [Antibody Sequencing]

In order to determine the monoclonal antibody sequence, one monoclone 5A2F9-4 was selected for sequencing. Total RNA was isolated from hybridoma cells according to the technical manual of TRIzol reagent. The total RNA was then reverse transcribed into cDNA using isotype-specific antisense primers or universal primers, according to the PrimeScript TM First Strand cDNA Synthesis Kit Technical Manual. Antibody fragments of VH and VL were amplified according to the standard operating procedure (SOP) method of rapid amplification of cDNA ends (RACE) of GenScript. The amplified antibody fragments were cloned into standard cloning vectors, respectively. Colony PCR was performed to screen for clones containing inserts of the correct size. At least 5 colonies with the correct size inserts were sequenced. The sequences of the different clones were aligned to determine the consensus sequence of these clones.

The DNA sequence of VH is thus determined as shown in SEQ ID NO:10; the DNA sequence of VL is determined as shown in SEQ ID NO:11. The leader sequence is underlined by a dashed line, and the CDR sequence is underlined by a solid line.

(SEQ ID NO: 10)
Leader sequence-FR1-CDR1-FR2-CDR2-FR3-CDR3-FR4
ATGGGATGGAGCTATATCATCCTCTTTTTGGTAGCAACAGCTACAGATGT

CCACTCCCAGGTCCAACTGCAGCAGCCTGGGGCTGAACTGGTGAAGCCTG

GGGCTTCAGTGAAGCTGTCCTGCAAGGCTTCTGGCTACACCTTCACCAGC

TACTGGATGCACTGGGTGAAGCAGAGGCCTGGACAAGGCCTTGAGTGGAT
    CDR1

TGGAGAGATTAATCCTAGGAACGGTCGTATTAACCAGAATGAGAAGTTCA

AGAGCAAGGCCACACTGACTGTAGCCAAATCCTCCAGCACGGCCTACATG
    CDR2

CAACTCAGCAGCCTGACATCTGAGGACTCTGCGGTCTATTACTGTTCAAG

AGGGGGCGGTAGTAGCGCGGAGGGGGGCTACTGGGGCCAAGGCACCACTC
        CDR3

TCACAGTCTCCTCA (SEQ ID NO: 11)
Leader sequence-FR1-CDR1-FR2-CDR2-FR3-CDR3-FR4
ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCATCTCTTGCAGATCTAGTCAGAGCATTGTACAT

AGTAATGGAAACACCTATTTAGATTGGTACCTGCAGAAACCAGGCCAGTC
    CDR1

TCCAAAGCTCCTGATATACAAAGTTTTCAACCGACTTTCTGGGGTCCCAG
                    CDR2

ACAGGTTCAGTGGCAGTGGATCAGGGACAGATTTCACACTCAAGATCAGC

AGAGTGGAGGCTGAGGATCTGGGAGTTTATTACTGCTTTCAAGGTTCACA
                                        CDR3

TGTTCCTCTCACGTTCGGTGCCGGGACCAAGCTGGAGCTGCAA

The amino acid sequences of VH and VL can be deduced from the DNA sequences. The amino acid sequence of VH is shown in SEQ ID NO:2, and the amino acid sequence of VL is shown in SEQ ID NO:3. The leader sequence is underlined by a dashed line, and the CDR sequence is underlined by a solid line.

(SEQ ID NO: 2)
Leader sequence-FR1-CDR1-FR2-CDR2-FR3-CDR3-FR4
MGWSYIILFLVATATDVHSQVQLQQPGAELVKPGASVKLSCKASGYTFTS

YWMHWVKQRPGQGLEWIGEINPRNGRINQNEKFKSKATLTVAKSSSTAYM
    CDR1                CDR2

QLSSLTSEDSAVYYCSRGGGSSAEGGYWGQGTTLTVSS
                CDR3

(SEQ ID NO: 3)
Leader sequence -FR1-CDR1-FR2-CDR2-FR3-CDR3-FR4
MKLPVRLLVLMFWIPASSSDVLMTQTPLSLPVSLGDQASISCRSSQSIVH

SNGNTYLDWYLQKPGQSPKLLIYKVFNRLSGVPDRFSGSGSGTDFTLKIS
    CDR1                CDR2

RVEAEDLGVYYCFQGSHVPLTFGAGTKLELQ
            CDR3

It can be deduced that the RNA sequence encoding VH is SEQ ID NO:12, and the RNA sequence encoding VL is SEQ ID NO:13.

Example 4 [Specificity Test of Antibody]

4.1 Preparation of hNav1.9 Antigen

The human Nav1.9-HA plasmid (7-8 μg) was transfected into ND7/23 cells (10 cm cell dishes), cultured at 37° C. for 10 hours, and then cultured in a cell dish at 29° C. for 20 hours to collect cells ND7/23: HA-h Nav1.9.

The HA tag plasmid was transfected into COS-7 cells in the same manner to obtain COS-7: HA-M cells.

4.2 Western Blotting Analysis

1. The cell culture medium was aspirated, 2 ml of sterilized PBS was added and the cell dish was gently rotated to wash the cells twice.

2. 1 ml of Western and IP cell lysate were added, and the cells were collected by cell scraper and lysed on ice for half an hour.

3. A sonicator was used for ultrasonically disruption twice for 3 s each time.

4. The cell lysate was centrifuged at 12000 rpm for 10 minutes at 4° C. to collect the cell lysis supernatant.

5. 40 μl of the supernatant of the cell lysate was taken and electrophoresed on an 8% SDS-polyacrylamide gel.

6. After transformation, the cells were incubated with HA tag (1:2000) antibody and 5A2F9-4 (1:300) antibody for 1 hour at room temperature.

7. The cells were washed three times with PBS for 5 minutes each time;

8. A digoxigenin-labeled anti-mouse antibody (1:20000) was added and incubated for 1 hour at room temperature;

9. The cells were washed three times with PBS for 5 minutes each time;

10. A digoxin substrate was added and developed for 5-10 minutes.

11. Western blot hybridization was performed.

4.3 Western Hybridization Results

Figure 4:
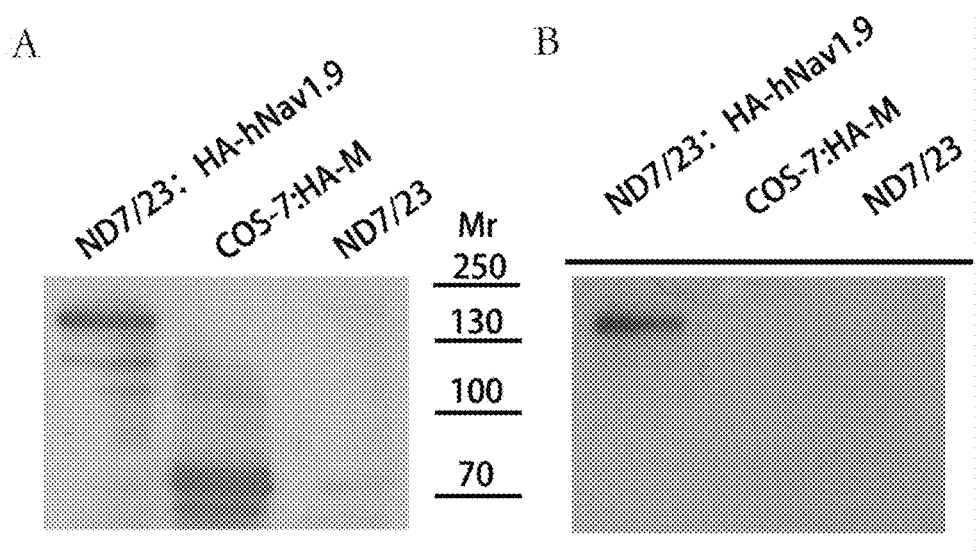

As can be seen from FIG. 4, the 5A2F9-4 antibody and the HA-tagged antibody can produce a hybridization signal between 130-250 KD, while no corresponding signal was detected in the negative control, and the hybridization signal was close to the molecular weights of hNav1.9 being about 210 kDa, indicating that the antibody can recognize the protein of hNav1.9.

Example 5 [Analgesic Efficacy of 5A2F9-4 Antibody in Wild-Type Mice]

In order to test whether the 5A2F9-4 antibody has an analgesic effect, we used Formalin inflammatory pain model to evaluate the efficacy of 5A2F9-4 antibody. After intravenous injection of the antibody, 20 μl of 5% formalin was injected to the mice hind paw after 30 minutes injection of the antibody. The time of paw licking and withdrawal of the mice was recorded every 5 minutes, to evaluate the analgesic efficacy of different treatments on Formalin-induced spontaneous inflammatory pain.

5.1 Experimental Steps

According to the method of Lee et al. (2014, Cell 157, 1393-1404), 12 wild-type mice were tested after 2 days of adaptation. They were randomly divided into 2 groups, one served as control group, injected with PBS by tail vein, and the other served as experimental group, injected with 10 mg/kg of 5A2F9-4 antibody by tail vein. After half an hour, 20 μL of 5% Formalin was injected subcutaneously into the hind paw to produce pain caused by acute inflammation, and the times of paw licking and withdrawal was recorded every 5 minutes for a total of 45 minutes. Phase I (0-10 minutes) and phase II (10-45 minutes) were statistically analyzed, respectively. Phase I represented acute pain, and phase II represented spontaneous persistent pain. After the experiment, the two phases as well as the differences between the drug injection group and the control group during various phases in the wild-type mice were statistically analyzed.

5.2 Experimental Results

As shown in FIG. 5, the wild-type mice were injected with 5A2F9-4 antibody by tail vein, and given 5% Formalin to induce acute inflammatory pain. The antibody can reduce the total time of hind paw licking within 10-15 minutes and 30-40 minutes after subcutaneous injection of 5% Formalin, namely, the total time of paw licking in Phase II, which was significantly different compared to that of the negative control. The results showed that 5A2F9-4 antibody can alleviate phase II inflammatory pain induced by 5% Formalin in wild type mice, which is equivalent to the reported effect in the literature.

```
Sequence list:

Leu Asn Ser Phe Ser Asn Glu Glu Arg Asn Gly Asn
Leu Glu (SEQ ID NO: 1)

Met Gly Trp Ser Tyr Ile Ile Leu Phe Leu Val Ala
Thr Ala Thr Asp Val His Ser Gln Val Gln Leu Gln
Gln Pro Gly Ala Glu Leu Val Lys Pro Gly Ala Ser
Val Lys Leu Ser Cys Lys Ala Ser Gly Tyr Thr Phe
Thr Ser Tyr Trp Met His Trp Val Lys Gln Arg Pro
Gly Gln Gly Leu Glu Trp Ile Gly Glu Ile Asn Pro
Arg Asn Gly Arg Ile Asn Gln Asn Glu Lys Phe Lys
Ser Lys Ala Thr Leu Thr Val Ala Lys Ser Ser Ser
Thr Ala Tyr Met Gln Leu Ser Ser Leu Thr Ser Glu
Asp Ser Ala Val Tyr Tyr Cys Ser Arg Gly Gly Gly
Ser Ser Ala Glu Gly Gly Tyr Trp Gly Gln Gly Thr
Thr Leu Thr Val Ser Ser (SEQ ID NO: 2)

Met Lys Leu Pro Val Arg Leu Leu Val Leu Met Phe
Trp Ile Pro Ala Ser Ser Ser Asp Val Leu Met Thr
Gln Thr Pro Leu Ser Leu Pro Val Ser Leu Gly Asp
Gln Ala Ser Ile Ser Cys Arg Ser Ser Gln Ser Ile
Val His Ser Asn Gly Asn Thr Tyr Leu Asp Trp Tyr
Leu Gln Lys Pro Gly Gln Ser Pro Lys Leu Leu Ile
Tyr Lys Val Phe Asn Arg Leu Ser Gly Val Pro Asp
Arg Phe Ser Gly Ser Gly Ser Gly Thr Asp Phe Thr
Leu Lys Ile Ser Arg Val Glu Ala Glu Asp Leu Gly
Val Tyr Tyr Cys Phe Gln Gly Ser His Val Pro Leu
Thr Phe Gly Ala Gly Thr Lys Leu Glu Leu Gln
(SEQ ID NO: 3)
```

```
Sequence list:

Ser Tyr Trp Met His (SEQ ID NO: 4)

Glu Ile Asn Pro Arg Asn Gly Arg Ile Asn Gln Asn
Glu Lys Phe Lys Ser (SEQ ID NO: 5)

Gly Gly Gly Ser Ser Ala Glu Gly Gly Tyr
(SEQ ID NO: 6)

Arg Ser Ser Gln Ser Ile Val His Ser Asn Gly Asn
Thr Tyr Leu Asp (SEQ ID NO: 7)

Lys Val Phe Asn Arg Leu Ser (SEQ ID NO: 8)

Phe Gln Gly Ser His Val Pro Leu Thr (SEQ ID NO: 9)

atgggatgga gctatatcat cctcttttg gtagcaacag
ctacagatgt ccactcccag gtccaactgc agcagcctgg
ggctgaactg gtgaagcctg gggcttcagt gaagctgtcc
tgcaaggctt ctggctacac cttcaccagc tactggatgc
actgggtgaa gcagaggcct ggacaaggcc ttgagtggat
tggagagatt aatcctagga acggtcgtat taaccagaat
gagaagttca agagcaaggc cacactgact gtagccaaat
cctccagcac ggcctacatg caactcagca gcctgacatc
tgaggactct gcggtctatt actgttcaag aggggggcggt
agtagcgcgg aggggggcta ctggggccaa ggcaccactc
tcacagtctc ctca (SEQ ID NO: 10)

atgaagttgc ctgttaggct gttggtgctg atgttctgga
ttcctgcttc cagcagtgat gttttgatga cccaaactcc
actctccctg cctgtcagtc ttggagatca agcctccatc
tcttgcagat ctagtcagag cattgtacat agtaatggaa
acacctattt agattggtac ctgcagaaac caggccagtc
tccaaagctc ctgatataca aagtttttcaa ccgactttct
ggggtcccag acaggttcag tgcagtgga tcagggacag
atttcacact caagatcagc agagtggagg ctgaggatct
gggagtttat tactgctttc aaggttcaca tgttcctctc
acgttcggtg ccgggaccaa gctggagctg caa
(SEQ ID NO: 11)

augggaugga gcuauaucau ccucuuuuug guagcaacag
cuacagaugu ccacucccag guccaacugc agcagccugg
ggcugaacug gugaagccug gggcuucagu gaagcuguuc
ugcaaggcuu cuggcuacac cuucaccagc uacuggaugc
acuggguga gcagaggccu ggacaaggcc uugaguggau
uggagagauu aaaccuagga acggucguau uaaccagaau
gagaaguuca agagcaaggc cacacugacu guagccaaau
ccuccagcac ggccuacaug caacucagca gccugacauc
ugaggacucu gcggucuauu acuguucaag aggggggcggu
aguagcgcgg aggggggcua cuggggccaa ggcaccacuc
ucacagucuc cuca (SEQ ID NO: 12)

augaaguugc cuguuaggcu guuggugcug auguucugga
uuccugcuuc cagcagugau guuuugauga cccaaacucc
acucucccug ccugucaguc uuggagauca agccuccauc
ucuugcagau cuagucagag cauuguacau aguaauggaa
acaccuauuu agauugguac cugcagaaac caggccaguc
uccaaagcuc cugauauaca aaguuuucaa ccgacuuucu
gggguccag acagguucag ugcagugga ucagggacag
auuucacacu caagaucagc agaguggagg cugaggaucu
gggaguuuau uacugcuuuc aaguucaca uguuccucuc
acguucggug ccgggaccaa gcuggagcug caa
(SEQ ID NO: 13)
```

What is claimed is:

1. An antibody or antibody fragment thereof that specifically binds to a cytomembrane voltage-gated sodium ion channel α subunit Nav1.9, wherein:
   the heavy chain variable region of the antibody or antibody fragment thereof comprises CDR sequences of CDRH1 as shown in SEQ ID NO.4, CDRH2 as shown in SEQ ID NO.5 and CDRH3 as shown in SEQ ID NO.6; and
   the light chain variable region of the antibody or antibody fragment thereof comprises CDR sequences of CDRL1 as shown in SEQ ID NO.7, CDRL2 as shown in SEQ ID NO.8, and CDRL3 as shown in SEQ ID NO.9.

2. The antibody or antibody fragment thereof according to claim 1, wherein the antibody or antibody fragment comprises a heavy chain variable region as shown in SEQ ID NO.2 and/or a light chain variable region as shown in SEQ ID NO.3.

3. The antibody or antibody fragment thereof according to claim 1, wherein the antibody further comprises an antibody constant region.

4. The antibody or antibody fragment thereof according to claim 3, wherein the antibody constant region comprises an IgM, IgD, IgG, IgA or IgE antibody constant region.

5. The antibody or antibody fragment thereof according to claim 1, wherein the antibody or antibody fragment is in a structural form selected from the group consisting of a full antibody, Fab, F(ab')2, dsFv, scFv, a diabody, a minibody, a bispecific antibody, a multi-specific antibody, a chimeric antibody, and a CDR-grafted antibody.

6. The antibody or antibody fragment thereof according to claim 1, wherein the antibody is a monoclonal antibody.

7. A pharmaceutical composition comprising the antibody or antibody fragment thereof according to claim 1.

8. A method for treating or relieving pain in a pain-related disease, comprising administering to an individual in need thereof an antibody or antibody fragment thereof according to claim 1.

* * * * *